United States Patent
Intini et al.

(12) 
(10) Patent No.: US 6,458,983 B1
(45) Date of Patent: Oct. 1, 2002

(54) METHOD FOR SYNTHESIZING COMPLEXES OF PLATINUM WITH IMINOETHERS AND THEIR USE AS ANTITUMORAL DRUGS AND NUCLEOTIDE-BASE MODIFIERS

(75) Inventors: Francesco Paolo Intini, Bari; Giovanni Natile, Putignano; Angelina Boccarelli, Scansano Jonico; Mauro Coluccia, Bari, all of (IT)

(73) Assignee: Universita' Degli Studi di Bari, Bari (IT)

( * ) Notice: Subject to any disclaimer, the term of this patent is extended or adjusted under 35 U.S.C. 154(b) by 0 days.

(21) Appl. No.: 09/357,974

(22) Filed: Jul. 21, 1999

(30) Foreign Application Priority Data

Jul. 22, 1998 (IT) .......................................... MI98A1696

(51) Int. Cl.$^7$ ............................. C07F 15/00; C07F 15/02
(52) U.S. Cl. ...................... 556/136; 556/137; 556/143; 556/148; 536/25.3
(58) Field of Search ................................ 556/136, 137, 556/143, 148; 536/25.3

(56) References Cited

PUBLICATIONS

Coluccia et al., J. of Med. Chem., vol. 39, No. 4, pp. 510–512, Feb. 1993.*

Zaludova et al., Molecular Pharmacology, vol. 52, No. 3 pp. 354–361, Sep. 1997.*

Mehicic, M. et al.: "spectroscopic investigation of structure and bonding in dichlorobis (oxazole) platinum (ii) complexes, cis–(ptc12(oxa)2) and trans–(ptc12(oxa)2)" Journal of Physical Chemistry, vol. 88, 1984, pp. 581–586, XP000989513* compounds in Table I, and text in introduction section referring to reference 13*.

Michelin, R.A. et al.: "conversion of nitriles into d2–1, 3–oxazolines in platinum(ii) complexes. Crystal structure of trans (ptc12(n=c(but)och2ch2)2)" Journal of the Chemical Spociety, Dalton Transactions, 1993, pp. 959–966, XP000982601* compounds 1(a)–7(b)*.

Michelin, R.A. et al.: "synthesis of 5,6–dihydro–4h–1,3–oxazines from neutral and cationic platinum(ii) nitrile complexes. X–ray structure of trans–(pt(cf3)(n=c(ph)och2ch2ch2)(pph3)2)bf4" Inorganica Chimica Acta, vol. 220, 1994, pp. 21–33, XP000989597* compounds (1)–(6)*.

Michelin, R. A. et al.: "transition–metal–promoted cyclization reactions of nitrile ligands in complexes of platinum(ii): synthesis of 2–oxazoline derivatives and x–ray structure of cis–c12pt(n=c(ph)och2ch2)2" Organometallics, vol. 10, 1991, pp. 1751–1757, XP000989592 *compounds (1)–(4)*.

* cited by examiner

*Primary Examiner*—James O. Wilson
(74) *Attorney, Agent, or Firm*—Guido Modiano; Albert Josif; Daniel J. O'Byrne

(57) ABSTRACT

A process for synthesizing complexes of platinum(II) with iminoethers having the formula: $[Pt^{II}X_2(L)(L')]$, where X is a monoanionic ligand, L is an iminoether ligand and L' is an amine group or, exclusively for the case of cyclic iminoethers, a second iminoether ligand. The platinum(II) complexes according to the present invention are suitable for the production of medical remedies having a broad antitumoral spectrum. The complexes of platinum(II) with iminoethers according to the invention are furthermore suitable as agents for modifying nucleotide bases into antisense and/or antigene oligonucleotides.

29 Claims, No Drawings

METHOD FOR SYNTHESIZING COMPLEXES OF PLATINUM WITH IMINOETHERS AND THEIR USE AS ANTITUMORAL DRUGS AND NUCLEOTIDE-BASE MODIFIERS

BACKGROUND OF THE INVENTION

The present invention relates to a method for synthesizing complexes of platinum with iminoethers and to their use as antitumoral drugs and nucleotide-base modifiers.

Specifically, the present invention relates to a method for synthesizing complexes of platinum(II) with iminoethers and to their use both as broad-spectrum antitumoral drugs and as nucleotide-base modifiers in antisense and/or antigene oligonucleotides.

The inorganic compound cis-diaminodichloroplatinum (II) (cis-[PtCl$_2$(NH$_3$)$_2$], cis DDP, also commonly known as cisplatinum, is a molecule having an antitumoral action which has been widely used clinically, particularly for treating solid tumors.

The chemotherapeutic effect of cisplatinum arises from a biochemical mechanism which is still not entirely known and which, since the drug interacts with cell DNA, forming intra- and interstrand bifunctional adducts, is probably due to structural and functional changes associated with the formation of adducts, particularly intrastrand adducts between adjacent purines. On the basis of current knowledge, however, a significant contribution to the action of cisplatinum by adducts of the interstrand type cannot be ruled out.

It is known that initial structure-activity correlation studies concerning with platinum complexes having the general formula [Pt$^{II}$X$_2$A$_2$], where X is a leaving anionic group and A$_2$ are two monodentate amine ligands or a bidentate amine ligand, demonstrated that the compounds having an antitumoral activity had their X groups in a cis configuration and vice versa that the geometric isomer of cisplatinum, trans-[PtCl$_2$(NH$_3$)$_2$], trans-DDP, like other platinum complexes having X-group in trans geometry, had no antitumoral activity. Accordingly, in the past the search for cisplatinum derivatives characterized by lower systemic toxicity and by a different spectrum of activity was orientated almost exclusively toward cis-geometry compounds.

However, platinum complexes with a trans geometry of the leaving ligands have been recently identified which are characterized by antitumoral properties which have been verified in experimental systems in vitro and/or in vivo. In particular, the following are known among these complexes:

complexes having the general formula trans-[PtCl$_2$(L)(L')], where L, L' is pyridine, thiazole, quinoline. These compounds, particularly with reference to trans-[PtCl$_2$(pyridine)$_2$], have been shown to have a higher cytotoxic effect in vitro against tumor cells than trans-DDP;

complexes of platinum with iminoethers, with particular reference to the complex trans-[PtCl$_2$\{E-HN=C(OMe)Me\}$_2$], where E is the configuration of the iminoether group, indicating that the platinum and the methoxyl are in the trans position with respect to the C=N double bond. This complex has a cytotoxic in vitro effectiveness similar to that of cisplatinum and an antitumoral activity in vivo with respect to solid and lymphoproliferative murine tumors.

complexes of platinum(IV), with particular reference to an octahedral compound of platinum(IV) with trans geometry and having the formula trans-[PtCl$_2$(OH)$_2$(NH$_3$)\{NH$_2$(C$_6$H$_{11}$)\}] and analogs thereof, have shown antitumoral activity in vitro and in vivo.

Recently it has been found that known antitumoral platinum complexes having a trans geometry have an activity against cisplatinum-resistant tumor cells, thus providing new guidelines for research into platinum complexes having a different mechanism of action with respect to cisplatinum.

Biomedical technology currently uses synthetic oligonucleotides in order to achieve selective inhibition of gene expression for the analysis of specific genetic functions and for the possible pharmacological treatment of diseases caused by alterations of cell gene expression.

These synthetic oligonucleotides are known to be an elective class of drugs for regulating mRNA translation and DNA transcription, in antisense and antigene therapeutic strategies, respectively.

In order to improve the biological effectiveness of synthetic oligonucleotides, providing a stable and irreversible interaction with the target sequences, some chemical functional groups and/or photonically activated agents have been conjugated with synthetic oligonucleotides.

However, this model has been found to have drawbacks, mainly due, in the case of the presence of chemical functional groups, to the onset of non-sequence-specific association reactions, and due, in the case of the presence of photonically activated agents, to difficulty in application in in vivo systems.

SUMMARY OF THE INVENTION

A general aim of the present invention is to avoid or significantly reduce the disadvantages noted in the known art.

A primary object of the present invention is to provide new broad-spectrum antitumoral drugs whose administration entails reduced side effects.

Another object of the present invention is to provide platinum(II) complexes which can be used as agents for modifying nucleotide bases in antisense and/or antigene oligonucleotides which are highly specific and do not entail high production costs.

Another object is to provide a method for synthesizing complexes of platinum with iminoethers which is simple to perform.

In view of this aim, these objects and others which will become apparent hereinafter, according to the present invention, complexes of platinum(II) with iminoethers are provided, said complexes having the formula (I):

[Pt$^{II}$X$_2$(L)(L')]     (I), wherein
X is a monoanionic ligand, preferably a halide, more preferably selected from Cl$^-$ and I$^-$;
L is an iminoether group or ligand, preferably having the formula HN=C(OR')R, or the formula N=C(OR')—(CH$_2$)$_n$—CH$_2$, or the formula N=C(R)—O—(CH$_2$)$_n$—CH$_2$, wherein
R and R' are a linear or branched alkyl, preferably a lower alkyl, more preferably an alkyl containing 1 to 6 atoms of C or an aryl, said aryl preferably being a substituted or unsubstituted phenyl-group and
n=1, 2, 3;
L' is an amine group or ligand or, exclusively for the case of cyclic iminoethers, a second iminoether group.
Advantageously, said amine group is selected from ammonia, a primary or secondary aliphatic amine or an aromatic amine, such as piridine or quinoline, optionally substituted.

Platinum(II) complexes having the formula (I) according to the present invention can have a cis or trans geometry of the monoanionic ligands and of the aminic and iminoether ligands, with respect to the metallic center; moreover, the iminoether ligand HN=C(OR')R can have a different configuration (E or Z) according to the relative position (trans or cis) of the OR' group and of the metallic center with respect to the C=N double bond.

DESCRIPTION OF THE PREFERRED EMBODIMENTS

According to one embodiment of the present invention, said platinum(II) complexes have the following structure forms:

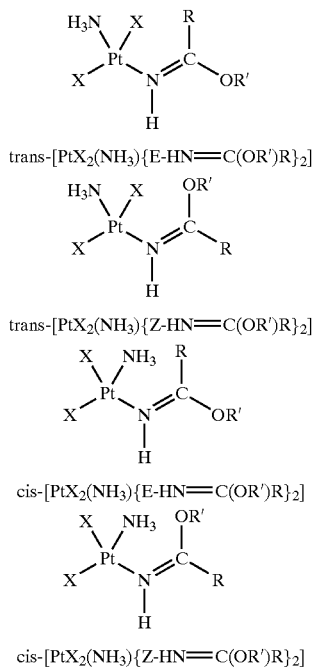

According to another aspect of the present invention, a process is provided for synthesizing compounds of platinum (II) with iminoethers having the formula [Pt$^{11}$X$_2$(L)(L')], wherein X is a monoanionic ligand, preferably a halide, more preferably selected from Cl$^-$ and I$^-$;

L is an iminoether group or ligand having the formula HN=C(OR')R or the formula

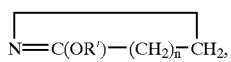

or the formula

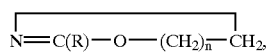

where R and R' are an alkyl or an aryl and n=1, 2, 3;

L' is an amine group or ligand or, exclusively for the case of cyclic iminoethers, a second iminoether group; said process comprising the steps of:

1) treatment of cis-[PtX$_2$(L')$_2$] in a mixture of water and nitrile (NCR) in order to obtain trans-[PtX$_2$(L') (NCR)];

2) treatment of trans-[PtX$_2$(L')(NCR)] with an alcohol and a base (a hydroxide of an alkaline/alkaline-earth metal) to produce trans-[PtX$_2$(L') (Z-L)];

3) transformation of the trans-[PtX$_2$(L')(Z-L)] into the isomer trans-[PtX$_2$(L')(E-L)] by reaction with a hydroxide of an alkaline/alkaline-earth metal in an alcohol;

4) in the case of cyclic iminoethers, the acyclic species initially formed [HN=C(O—(CH$_2$)$^n$CH$_2$X)R] or [HN=C(OR)—(CH$_2$)$_n$CH$_2$X] is subjected to a cyclization reaction in a basic environment, with elimination of HX and formation of

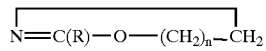

and

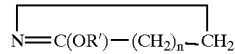

respectively;

5) reaction sequences 2, 3, 4 can be applied to the [PtX$_2$(NCR)$_2$] substrates in order to obtain the platinum(II) compounds with two anionic ligands (X) and two cyclic iminoether groups.

According to another aspect, the present invention relates to complexes of platinum(II) with iminoethers having the formula (I) for use as a medicament and/or to the use thereof for the manufacture of a medicament for treating tumours.

In particular, it has been verified that complexes of platinum(II) with iminoethers having the formula (I) have a marked antitumoral activity which has been confirmed in experimental systems in vitro and in vivo. In particular, the platinum complexes according to the invention have a broad antitumoral spectrum accompanied by reduced onset of side effects.

According to another aspect, the present invention relates to the use of complexes of platinum(II) with iminoethers having the formula (I) as agents for modifying the nucleotide bases into antisense and/or antigene oligonucleotides.

In particular, it has been found that the specific properties of interaction with DNA of the [Pt$^{11}$X$_2$(L)(L')] complexes with trans geometry of the L, L' ligands described above give antisense and/or antigene oligonucleotides, appropriately modified with the platinum complex, the ability to irreversibly bind to the complementary sequences of nucleic acids, thus being able to determine the inhibition of RNA translation and/or gene transcription.

The above complexes having the formula trans-[Pt$^{11}$X$_2$ (L)(L')], owing to their specific structure and chemical reactivity, can be used to selectively modify one of the nucleotide bases of an antisense and/or antigene oligonucleotide. In both cases, the platinum complex forms a stable adduct of the monofunctional type which rapidly becomes an intercatenary bifunctional adduct when the modified oligonucleotide associates with its complementary nucleic acid sequence.

The following examples are provided merely by way of illustration of the present invention and must not be understood as limiting the scope of the invention as defined by the accompanying claims.

EXAMPLE 1

A process for synthesizing the trans-[$PtCl_2(NH_3)$]{HN=C(OMe)Me}] platinum complex.

1) Preparation of trans-[$PtI_2(NH_3)(NCMe)$] starting from cis-[$PtI_2(NH_3)_2$].

The cis-[$PtI_2(NH_3)_2$] (1.000 g; 2.07 mmol) dissolved in a mixture of $H_2O$ (10 ml) and $CH_3CN$ (10 ml) is heated to 90° C. for 30 minutes, with coolant in countercurrent. The yellow solution is concentrated at 50° C.; the resulting dark yellow precipitate constitutes the required product. This is separated from the mother liquor, washed and dried. The mother liquor is dried out. The solid residue is treated with a small amount of $CH_3CN$, the initial product that did not react and is not soluble in NCR is isolated and returned to the reaction. The $CH_3CN$ solution is concentrated to a small volume and the precipitate is isolated. If the product is not pure, it is necessary to dissolve it in the smallest amount of acetone and make it precipitate again by adding water. The weight of the final complex is 0.766 g (1.51 mM, 73% yield).

2) Preparation of trans-[$Pt(NO_3)_2(NH_3)(NCMe)$] starting from trans-[$PtI_2(NH_3)(NCMe)$].

The trans-[$PtI_2(NH_3)(NCMe)$] (678.5 mg; 1.34 mmol) is dissolved in acetone (35 ml). This yellow solution receives the addition of $AgNO_3$ (456.0 mg; 2.68 mmol) dissolved in a few drops of water. The reaction mixture, protected from the light, is left under agitation for 2 hours, at the end of which the solution is filtered on a celite bed and dried.

The white solid residue of trans-[$Pt(NO_3)_2(NH_3)(NCMe)$] is highly unstable in light and heat; therefore it must be stored in a freezer as soon as it is obtained. The reaction is quantitative.

3) Synthesis of trans-[$PtCl_2(NH_3)(NCMe)$] starting from trans-[$Pt(NO_3)_2(NH_3)(NCMe)$].

The trans-[$Pt(NO_3)_2(NH_3)(NCMe)$] (0.505 g; 1.34 mmol) is dissolved in water (25 ml) at the temperature of 40–45° C. The dissolution process takes 10 minutes. The solution, after adding KCl (522.7 mg; 7.01 mmol) is kept for 30 minutes at the same temperature and then at 4° C. for 12 hours. A clear yellow precipitate is formed and is separated from the solution by filtration. Another dose of product is obtained from the mother liquor by concentration at 45° C. to approximately ⅓ of its volume. The trans-[$PtCl_2(NH_3)(NCMe)$] obtained weighs 300 mg (9.26 mmol). The yield of the reaction is 71%.

4) Reaction for the transformation of trans-[$PtCl_2(NH_3)(NCMe)$] to trans-[$PtCl_2(NH_3)${Z—HN=C(OMe)Me}].

A suspension of trans-[$PtCl_2(NH_3)(NCMe)$] (290 mg; 8.94 mmol) in 2.5 ml of MeOH is treated with 100 mg of KOH. The system is left to react for 30 minutes at 0° C. The final product has a yellow color and is isolated from the solution by filtration, washed with cold water and dried in a dry air stream. The product is found to be trans-[$PtCl_2(NH_3)${Z-HN=C(OMe)Me}] (261 mg). The yield of the reaction is 82%.

5) Reaction for the Transformation of the Isomer Trans-[$PtCl_2(NH_3)${Z-HN=C(OMe)Me}] to the Isomer Trans-[$PtCl_2(NH_3)${E-HN=C(OMe)Me}].

The trans-[$PtCl_2(NH_3)${Z-HN=C(OMe)Me}] (150 mg; 0.42 mM) is reacted with KOH (28 mg; 0.49 mM) in MeOH (6 ml) for 6 hours. The solution is slightly turbid and dark. At the end of the specified time, the solution is neutralized with concentrated HCl and dried. The resulting product is extracted with $CH_2Cl_2$, in which the KCl is not soluble, then the solution is filtered and the solvent is evaporated. The solid residue, predominantly constituted by the E isomer, is purified by silica column chromatography using as eluent a mixture of $CH_2Cl_2$ and $CH_3COCH_3$ with an increasing composition of acetone.

EXAMPLE 2

The antitumoral activity of compounds having the formula trans-[$PtCl_2(NH_3)${Z-HN=C(OMe)Me}] (1) and trans-[$PtCl_2(NH_3)${E-HN=C(OMe)Me}] (2) was tested. Specifically, the antitumoral activity of compounds (1) and (2) was analyzed in experimental systems in vitro, testing for inhibition of the proliferation of human tumor cells in culture and in vivo by testing the increment in survival of mice carriers of P388 murine leukemia.

The inhibitory effect of compounds (1) and (2) on the in vitro proliferation of human tumor cells of ovarian carcinoma (A2780), pulmonary carcinoma (Calu), colon carcinoma (LoVo) and on an ovarian carcinoma line (A2780/cp8) with resistance to cisplatinum is presented in the following Table I.

Proliferation inhibition is expressed by means of $IC_{50}$ values, which indicate the concentration of compound ($\mu M$) in the culture medium that determines a 50% reduction in the proliferation of the treated cells with respect to untreated cells.

TABLE I

Inhibitory concentrations ($IC_{50}$) of compounds 1 and 2 on human tumor cells.

| Compound | A2780 | Calu | Lo Vo | A2780/cp8 |
|---|---|---|---|---|
| 1 | 37 | 90 | 21 | 35 |
| 2 | 8.5 | 55 | 7 | 8.6 |

The $IC_{50}$ values were extrapolated from dose-response curves obtained by treating for 72 hours the tumor cells with various concentrations of the tested compounds dissolved in the culture medium and checking, at the end of the incubation period, the number of cells present in the treated samples with respect to the number of cells in the untreated samples (control).

The antitumoral activity in vivo of compounds 1 and 2, expressed as an increment in the survival of P388 murine leukemia carrier mice, was also tested. The extrapolated data are listed hereafter.

TABLE II

Antitumoral activity in vivo of platinum compounds with respect to P388 murine leukaemia[a].

| Compound | Dosage (mg/kg/g; days 1–8) | Percentage variation of body weight[b] | ILS[c] |
|---|---|---|---|
| 1 | 10 | −1.5 | 165 |
|   | 15 | −4.4 | 173 |
|   | 20 | −11.5 | 190[d] |

TABLE II-continued

Antitumoral activity in vivo of platinum compounds with respect to P388 murine leukaemia[a].

| Compound | Dosage (mg/kg/g; days 1–8) | Percentage variation of body weight[b] | ILS[c] |
|---|---|---|---|
| 2 | 10 | −1.8 | 128 |
|   | 15 | −3.1 | 152 |
|   | 20 | −10 | 132[e] |
| Solvent (NaCl 0.9%) | — | +5.5 | — |

[a]P388 leukaemic cells ($10^6$/animal) were inoculated in the peritoneum in B6D2F1 female mice (body weight = 18 g) on day 0; treatment with the platinum compounds, dissolved at the time of use in a physiological solution, was performed on days 1–7, administering IP the doses indicated in the table in a volume equal to 0.1 ml/10 g body weight.
[b]Percentage variation of body weight of the animals at the end of the treatment.
[c]ILS = (average of the days of survival of treated mice/average of days of survival of untreated mice) × 100.
[d]ILS calculated on 4 animals; 2/6 mice showed a survival of over 120 days and are considered cured.
[e]ILS calculated on 4 animals, 2/6 mice having died due to toxicity during the treatment.

[a] P388 leukemic cells ($10^6$/animal) were inoculated in the peritoneum in B6D2F1 female mice (body weight=18 g) on day 0; treatment with the platinum compounds, dissolved at the time of use in a physiological solution, was performed on days 1–7, administering IP the doses indicated in the table in a volume equal to 0.1 ml/10 g body weight.

[b] Percentage variation of body weight of the animals at the end of the treatment.

[c] ILS=(average of the days of survival of treated mice/average of days of survival of untreated mice) X 100.

[d] ILS calculated on 4 animals; 2/6 mice showed a survival of over 120 days and are considered cured.

[e] ILS calculated on 4 animals, 2/6 mice having died due to toxicity during the treatment.

The disclosures in Italian Patent Application No. M198A001696 from which this application claims priority are incorporated herein by reference.

What is claimed is:

1. Complexes of platinum(II) with iminoethers having the formula:

$$\{Pt^{II}X_2(L)(L')\},$$

wherein
X is a monoanionic ligand;
L is an iminoether ligand;
L' is an amine group.

2. Complexes according to claim 1, wherein said monoanionic ligand is Cl⁻ or I⁻.

3. Complexes according to claim 1, wherein said iminoether ligand has the formula HN=C(OR')R, wherein R and R' are an alkyl or an aryl.

4. Complexes according to claim 3, wherein said iminoether is cyclic and has the formula N=C(OR')—(CH$_2$)$_n$—CH$_2$, or N=C(R)—O—(CH$_2$)$_n$—CH$_2$, where R and R' are an alkyl or an aryl and n=1, 2 and 3.

5. Process for the synthesis of platinum(II) compounds with iminoethers having the formula:

$$\{Pt^{II}X_2(L)(L')\}$$

wherein
X is a monoanionic ligand;
L is an iminoether group or ligand having the formula HN=C(OR')R,
L' is an amine group,
said process comprising the steps of:
 1) providing a nitrile trans-{PtX$_2$(L')(NCR)}, or {(PtX$_2$(NCR)$_2$};
 2) transformation of the nitrile trans-{PtX$_2$(L')NCR)} or {PtCl$_2$(NCR)$_2$} into the corresponding iminoether;
 3) isomerization of the isomer trans-{PtX$_2$(L')(Z-L)} into the isomer trans-{PtX$_2$(L')(E-L)} by treatment with an alcohol in a basic environment;
 4) cyclization of the acyclic iminoethers {H=C(O—CH$_2$)$_n$CH$_2$X)—R} and {HN=C(OR)—(CH$_2$)$_n$CH$_2$X} into the cyclic iminoethers by cyclization reaction in a basic environment in which HX elimination and formation of N=C(OR")—(CH$_2$)$_n$—CH$_2$ and N=C(R)—O—(CH$_2$)$_n$—CH$_2$ occurs;
 5) transformation of trans-PtX$_2$(L')(Z-L)} into the isomer trans-{PtX$_2$(L')(E-L)}.

6. A process according to claim 5, wherein the step 1) is performed under heating.

7. A process according to claim 5, wherein step 5) comprises the reaction of trans-[PtX$_2$(L')(Z-L)] with KOH in MeOH.

8. A medicament comprising a therapeutically effective amount of a complex of platinum(II) with iminoethers having the formula:

$$\{Pt^{II}X_2(L)(L')\}$$

wherein
X is a monoanionic ligand,
L is an iminoether ligand,
L' is an amine ligand,
in association with a pharmaceutically acceptable carrier.

9. Complexes according to claim 8, wherein said monoanionic ligand is Cl⁻ or I⁻.

10. Complexes according to claim 8, wherein said iminoether ligand has the formula HN=C(OR')R, wherein R and R' are an alkyl containing 1 to 6 C or an aryl.

11. Complexes according to claim 10, wherein R is methyl.

12. A method for modifying nucleotide bases into antisense and/or atigene oligonucleotides comprising contacting nucleotide bases with complexes of platinum(II) with iminoethers having the formula {Pt$^{II}$X$_2$(L)(L')} wherein X is a monoanionic ligand,
L is an iminoether ligand,
L' is an amine ligand.

13. Method according to claim 12, wherein said monoanionic ligand is Cl⁻ or I⁻.

14. Method according to claim 12, wherein said iminoether ligand has the formula HN=C(OR')R, wherein R and R' are an alkyl containing 1 to 6 C or an aryl.

15. Method according to claim 12, wherein R is methyl.

16. Complexes of platinum(II) with iminoethers having the formula:

$$\{Pt^{II}X_2(L)(L')\},$$

wherein
X is a monoanionic ligand;
L is a cyclic iminoether ligand of formula N=C(OR')—(CH$_2$)$_n$—CH$_2$, or N=C(R)—O—(CH$_2$)$_n$—CH$_2$, where R and R' are an alkyl or an aryl and n=1, 2 and 3;
L' is a second iminoether ligand.

17. Complexes according to claim 16, wherein said monoanionic ligand is Cl⁻ or I⁻.

18. Complexes according to claim 16, wherein said iminoether ligand has the formula HN=C(OR')R, wherein R and R' are an alkyl or an aryl.

19. Process for the synthesis of platinum(II) compounds with iminoethers having the formula:

$$\{Pt^{II}X_2(L)(L')\}$$

wherein

X is a monoanionic ligand;

L is a cyclic iminoether ligand of formula N=C(OR')—$(CH_2)_n$—$CH_2$, or N=C(R)—O—$(CH_2)_n$—$CH_2$, where R and R' are an alkyl or an aryl and n=1, 2 and 3;

L' is a second iminoether group, said process comprising the steps of:
1) providing anitrile trans-$\{PtX_2(L')NCR)\}$, or $\{PtX_2(NCR)_2\}$;
2) transformation of the anitrile trans-$\{PtX_2(L')(NCR)\}$ or $\{PtCl_2(NCR)_2\}$ into the corresponding iminoether;
3) isomerization of the isomer trans-$\{PtX_2(L')(Z-L)\}$ into the isomer trans-$\{(PtX_2(L')(E-L)\}$ by treatment with an alcohol in a basic environment;
4) cyclization of the acyclic iminoethers $\{HN=C(O-(CH_2)_nCH_2X)R\}$ and $\{HN=C(OR)-(CH_2)_nCH_2X\}$ into the cyclic iminoethers by cyclization reaction in a basic environment in which HX elimination and formation of N=C(OR')—$(CH_2)_n$—$CH_2$ and N=C(R)—O—$(CH_2)_n$—$CH_2$ occurs.
5) transformation of trans-$PtX_2(L')(Z-L)\}$ into the isomer trans-$\{PtX_2(L')(E-L)\}$.

20. A process according to claim 19, wherein the step 1) is performed under heating.

21. A process according to claim 19, wherein step 5) comprises the reaction of trans-$\{(PtX_2(L')(Z-L)\}$ with KOH in MeOH.

22. A medicament comprising a therapeutically effective amount of a complex of platinum(II) with iminoethers having the formula:

$$\{Pt^{II}X_2(L)(L')\}$$

wherein

X is a monoanionic ligand,

L is a cyclic iminoether ligand of formula N=C(OR')—$(CH_2)_n$—$CC_2$, or N=C(R)—O—$(CH_2)_n CH_2$, where R and R' are an alkyl or an aryl and n=1, 2 and 3, L' is a second iminoether ligand, in association with a pharmaceutically acceptable carrier.

23. Complexes according to claim 22, wherein said monoanionic ligand is Cl⁻ or I⁻.

24. Complexes according to claim 22, wherein said iminoether ligand has theformula HN=C(OR')R, wherein R and R' are an alkyl containing 1 to 6 C or an aryl.

25. Complexes according to claim 24, wherein R is methyl.

26. A method for modifying nucleotide bases into antisense and/or antigene oligonucleotides comprising contacting the nucleotide bases with complexes of platinum(II) with iminoethers having the formula $\{Pt^{II}X_2(L)(L')\}$ wherein X is a monoaniotic ligand, L is a cyclic iminoether ligand of formula N=C(OR')—$(CH_2)_n$—$CH_2$, or N=C(R)—O—$(CH_2)_n$—$CH_2$, where R and R' are an allyl or au aryl and n=1, 2 and 3, L' is a second iminoether ligand.

27. Method according to claim 26, wherein said monoanionic ligand is Cl³¹ or I⁻.

28. Method according to claim 26, wherein said iminoether ligand has the formula HN=C(OR')R, wherein R and R' are an alkyl containing 1 to 6 C or an aryl.

29. Method according to claim 26, wherein R is methyl.

* * * * *